US008066656B2

(12) United States Patent
Bonutti et al.

(10) Patent No.: US 8,066,656 B2
(45) Date of Patent: Nov. 29, 2011

(54) RANGE OF MOTION DEVICE

(75) Inventors: Boris P. Bonutti, Effingham, IL (US); Peter M. Bonutti, Effingham, IL (US); Kevin R. Ruholl, Effingham, IL (US); Glen A. Phillips, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 80 days.

(21) Appl. No.: 11/261,424

(22) Filed: Oct. 28, 2005

(65) Prior Publication Data

US 2007/0100267 A1 May 3, 2007

(51) Int. Cl.
*A61F 5/00* (2006.01)

(52) U.S. Cl. .......................................... 602/23; 602/30

(58) Field of Classification Search .................... 602/23, 602/27–30; 482/79

See application file for complete search history.

(56) References Cited

U.S. PATENT DOCUMENTS 432,327 A 7/1890 Page
433,227 A 7/1890 Beacock
2,191,283 A 2/1940 Longfellow
2,206,902 A 7/1940 Kost
2,223,276 A 11/1940 Ward
2,237,252 A 4/1941 Longfellow
2,246,689 A 6/1941 Kost
2,250,493 A * 7/1941 Milne ............................ 482/79
2,590,729 A 3/1952 Scognamillo
2,590,739 A 3/1952 Wahner et al.
2,811,154 A 10/1957 Scholl
2,820,455 A 1/1958 Hall
2,829,562 A 4/1958 La Rue
2,832,334 A 4/1958 Whitelaw
3,083,708 A 4/1963 Gottfried
3,338,237 A 8/1967 Sconce
3,351,055 A 11/1967 Gottfried
3,548,818 A 12/1970 Kaplan
3,580,248 A 5/1971 Larson
3,698,389 A 10/1972 Guedel
3,701,349 A 10/1972 Larson
3,724,452 A 4/1973 Nitschke
3,760,056 A 9/1973 Rudy
3,795,243 A 3/1974 Miller
3,811,434 A 5/1974 Jacobson et al.

(Continued)

FOREIGN PATENT DOCUMENTS

CA 2066151 10/1992

(Continued)

OTHER PUBLICATIONS

Written Opinion, PCT Search Report.

(Continued)

*Primary Examiner* — Michael A. Brown

(74) *Attorney, Agent, or Firm* — Armstrong Teasdale LLP

(57) ABSTRACT

The present invention provides an orthosis for stretching tissue around a joint of a patient between first and second relatively pivotable body portions. The orthosis includes a first member affixable to the first body portion and including a first extension member extending therefrom. A second member affixable to the second body portion is also included and has a second extension member having an arcuate shape extending therefrom. The second extension member is operatively connected to the first extension member and travels through the first extension member along an arcuate path when the second arm member is moved from a first position to a second position relative to the first arm member.

28 Claims, 9 Drawing Sheets

U.S. PATENT DOCUMENTS

| | | | |
|---|---|---|---|
| 3,814,419 | A | 6/1974 | Bjorklund et al. |
| 3,832,997 | A * | 9/1974 | Cappelletti .................... 602/11 |
| 3,856,004 | A | 12/1974 | Cox |
| 3,955,565 | A | 5/1976 | Johnson, Jr. |
| 3,970,316 | A | 7/1976 | Westmoreland, Jr. |
| 3,976,057 | A | 8/1976 | Barclay |
| 4,039,183 | A | 8/1977 | Sakurada |
| 4,076,022 | A | 2/1978 | Walker |
| 4,084,267 | A | 4/1978 | Zadina |
| 4,108,170 | A | 8/1978 | Spann |
| 4,180,870 | A | 1/1980 | Radulovic et al. |
| 4,214,577 | A | 7/1980 | Hoy |
| 4,229,001 | A | 10/1980 | Roman |
| 4,237,873 | A | 12/1980 | Terry et al. |
| 4,241,731 | A | 12/1980 | Pauley |
| 4,273,113 | A | 6/1981 | Hofstein |
| 4,285,773 | A | 8/1981 | Taciuk |
| 4,320,748 | A | 3/1982 | Racette et al. |
| 4,363,481 | A | 12/1982 | Erickson |
| 4,370,977 | A | 2/1983 | Mauldin et al. |
| 4,383,523 | A | 5/1983 | Schurman |
| 4,417,569 | A | 11/1983 | Brudny |
| 4,441,489 | A | 4/1984 | Evans et al. |
| 4,454,871 | A | 6/1984 | Mann et al. |
| 4,456,001 | A | 6/1984 | Pescatore |
| 4,456,002 | A | 6/1984 | Barber et al. |
| 4,502,470 | A | 3/1985 | Kiser et al. |
| 4,502,681 | A | 3/1985 | Blomqvist |
| 4,508,111 | A | 4/1985 | Hepburn |
| 4,509,509 | A | 4/1985 | Bouvet et al. |
| 4,538,595 | A | 9/1985 | Hajianpour |
| 4,538,600 | A | 9/1985 | Hepburn |
| 4,570,619 | A | 2/1986 | Gamm |
| 4,576,151 | A | 3/1986 | Carmichael et al. |
| 4,589,406 | A | 5/1986 | Florek |
| 4,606,542 | A | 8/1986 | Segal |
| 4,612,919 | A | 9/1986 | Best |
| 4,628,913 | A | 12/1986 | Lerman |
| 4,641,639 | A | 2/1987 | Padilla |
| 4,653,479 | A | 3/1987 | Maurer |
| 4,665,905 | A | 5/1987 | Brown |
| 4,693,239 | A | 9/1987 | Clover, Jr. |
| 4,716,889 | A | 1/1988 | Saringer |
| 4,718,665 | A | 1/1988 | Airy et al. |
| 4,727,865 | A | 3/1988 | Hill-Byrne |
| 4,739,334 | A | 4/1988 | Soref |
| 4,765,320 | A | 8/1988 | Lindemann et al. |
| 4,788,941 | A | 12/1988 | Villeneuve |
| 4,790,301 | A | 12/1988 | Silfverskiold |
| 4,793,334 | A | 12/1988 | McGuinness et al. |
| 4,805,601 | A | 2/1989 | Eischen, Sr. |
| 4,807,601 | A | 2/1989 | Wright |
| 4,809,688 | A | 3/1989 | Aymerica del Valle |
| 4,834,073 | A | 5/1989 | Bledsoe et al. |
| 4,844,094 | A | 7/1989 | Grim |
| 4,844,454 | A | 7/1989 | Rogers |
| 4,844,455 | A | 7/1989 | Funkhouser, Jr. |
| 4,848,326 | A | 7/1989 | Lonardo |
| 4,862,877 | A | 9/1989 | Barber |
| 4,865,024 | A | 9/1989 | Hensley et al. |
| 4,869,267 | A | 9/1989 | Grim et al. |
| 4,869,499 | A | 9/1989 | Schiraldo |
| 4,884,454 | A | 12/1989 | Johnson |
| 4,913,135 | A | 4/1990 | Mattingly |
| 4,913,755 | A | 4/1990 | Grim |
| 4,930,497 | A | 6/1990 | Saringer |
| 4,953,543 | A | 9/1990 | Grim et al. |
| 4,955,369 | A | 9/1990 | Bledsoe et al. |
| 4,955,396 | A | 9/1990 | Fralick et al. |
| 4,957,281 | A | 9/1990 | Christolear, Jr. |
| 4,964,402 | A | 10/1990 | Grim et al. |
| 4,991,234 | A | 2/1991 | Greenberg |
| 4,996,979 | A | 3/1991 | Grim et al. |
| 5,005,563 | A | 4/1991 | Veale |
| 5,018,514 | A | 5/1991 | Grood et al. |
| 5,019,050 | A | 5/1991 | Lynn et al. |
| 5,025,782 | A | 6/1991 | Salerno |
| 5,027,688 | A | 7/1991 | Suzuki et al. |
| 5,027,801 | A | 7/1991 | Grim |
| 5,027,802 | A | 7/1991 | Donohue |
| 5,036,837 | A | 8/1991 | Mitchell et al. |
| 5,036,838 | A | 8/1991 | Sherman |
| 5,052,375 | A | 10/1991 | Stark et al. |
| 5,070,866 | A | 12/1991 | Alexander et al. |
| 5,078,128 | A | 1/1992 | Grim et al. |
| 5,088,481 | A | 2/1992 | Darby |
| 5,100,403 | A | 3/1992 | Hotchkiss et al. |
| 5,102,411 | A | 4/1992 | Hotchkiss et al. |
| 5,116,359 | A | 5/1992 | Moore |
| 5,125,400 | A | 6/1992 | Johnson, Jr. |
| 5,135,470 | A | 8/1992 | Reeves |
| 5,139,475 | A | 8/1992 | Robicsek |
| 5,141,489 | A | 8/1992 | Sereboff |
| 5,156,589 | A | 10/1992 | Langen et al. |
| 5,163,451 | A | 11/1992 | Grellas |
| 5,167,612 | A | 12/1992 | Bonutti |
| 5,191,903 | A | 3/1993 | Donohue |
| 5,197,942 | A | 3/1993 | Brady |
| 5,201,702 | A | 4/1993 | Mars |
| 5,201,772 | A | 4/1993 | Maxwell |
| 5,203,321 | A | 4/1993 | Donovan et al. |
| 5,211,161 | A | 5/1993 | Stef |
| 5,213,094 | A | 5/1993 | Bonutti |
| 5,213,095 | A | 5/1993 | Dague |
| 5,218,954 | A | 6/1993 | van Bemmelen |
| 5,226,245 | A | 7/1993 | Lamont |
| 5,232,435 | A | 8/1993 | Leibinsohn |
| 5,252,101 | A | 10/1993 | Rosenwinkel et al. |
| 5,252,102 | A | 10/1993 | Singer et al. |
| 5,261,125 | A | 11/1993 | Cartwright et al. |
| 5,277,695 | A | 1/1994 | Johnson, Jr. et al. |
| 5,285,773 | A | 2/1994 | Bonutti et al. |
| 5,297,540 | A | 3/1994 | Kaiser et al. |
| 5,312,322 | A | 5/1994 | Santana |
| 5,316,022 | A | 5/1994 | Schiek, Sr. |
| 5,323,435 | A | 6/1994 | Baversten |
| RE34,661 | E | 7/1994 | Grim |
| 5,327,882 | A | 7/1994 | Saringer et al. |
| 5,328,448 | A | 7/1994 | Gray, Sr. |
| 5,329,705 | A | 7/1994 | Grim et al. |
| 5,348,530 | A | 9/1994 | Grim et al. |
| 5,349,956 | A | 9/1994 | Bonutti |
| 5,352,216 | A | 10/1994 | Shiono et al. |
| 5,354,260 | A | 10/1994 | Cook |
| 5,364,323 | A | 11/1994 | Liu |
| 5,365,947 | A | 11/1994 | Bonutti |
| 5,370,133 | A | 12/1994 | Darby et al. |
| 5,372,597 | A | 12/1994 | Hotchkiss et al. |
| 5,376,091 | A | 12/1994 | Hotchkiss et al. |
| 5,378,223 | A | 1/1995 | Grim et al. |
| 5,385,536 | A | 1/1995 | Burkhead et al. |
| 5,389,065 | A | 2/1995 | Johnson, Jr. |
| 5,391,132 | A | 2/1995 | Greenwald |
| 5,395,303 | A | 3/1995 | Bonutti et al. |
| 5,399,152 | A | 3/1995 | Habermeyer et al. |
| 5,403,265 | A | 4/1995 | Berguer et al. |
| 5,407,420 | A | 4/1995 | Bastyr et al. |
| 5,407,422 | A | 4/1995 | Matthijs et al. |
| 5,417,643 | A | 5/1995 | Taylor |
| 5,419,757 | A | 5/1995 | Daneshvar |
| 5,421,874 | A | 6/1995 | Pearce |
| 5,435,009 | A | 7/1995 | Schild et al. |
| 5,437,611 | A | 8/1995 | Stern |
| 5,452,205 | A | 9/1995 | Telepko |
| 5,453,075 | A | 9/1995 | Bonutti et al. |
| 5,453,082 | A | 9/1995 | Lamont |
| 5,456,268 | A | 10/1995 | Bonutti |
| 5,456,286 | A | 10/1995 | Warner et al. |
| 5,464,385 | A | 11/1995 | Grim |
| 5,466,213 | A | 11/1995 | Hogan et al. |
| 5,466,250 | A | 11/1995 | Johnson, Jr. et al. |
| 5,472,407 | A | 12/1995 | Schenck |
| 5,492,133 | A | 2/1996 | McVicker |
| 5,503,619 | A | 4/1996 | Bonutti |
| 5,503,622 | A | 4/1996 | Wehr |
| 5,503,908 | A | 4/1996 | Faass |
| 5,518,009 | A | 5/1996 | Ruiz-Gonzalez |

| | | | |
|---|---|---|---|
| 5,520,181 | A | 5/1996 | Kreidler et al. |
| 5,520,628 | A | 5/1996 | Wehr |
| 5,527,269 | A | 6/1996 | Reithofer |
| 5,531,669 | A | 7/1996 | Varnau |
| 5,535,274 | A | 7/1996 | Braitberg et al. |
| 5,538,486 | A | 7/1996 | France et al. |
| 5,571,077 | A | 11/1996 | Klearman et al. |
| 5,577,998 | A | 11/1996 | Johnson, Jr. et al. |
| 5,605,535 | A | 2/1997 | Lepage |
| 5,609,570 | A | 3/1997 | Lamont |
| 5,611,764 | A | 3/1997 | Bonutti et al. |
| 5,620,411 | A | 4/1997 | Schumann et al. |
| 5,626,537 | A | 5/1997 | Danyo et al. |
| 5,647,378 | A | 7/1997 | Farnum |
| 5,653,680 | A | 8/1997 | Cruz |
| 5,665,059 | A | 9/1997 | Klearman et al. |
| 5,681,269 | A | 10/1997 | Basaj et al. |
| 5,685,830 | A | 11/1997 | Bonutti |
| 5,755,679 | A | 5/1998 | Selner et al. |
| 5,761,834 | A | 6/1998 | Grim et al. |
| 5,772,619 | A | 6/1998 | Corbett |
| 5,778,565 | A | 7/1998 | Holt et al. |
| 5,788,659 | A | 8/1998 | Haas |
| 5,792,084 | A | 8/1998 | Wilson et al. |
| 5,820,577 | A | 10/1998 | Taylor |
| 5,823,975 | A | 10/1998 | Stark et al. |
| 5,833,639 | A | 11/1998 | Nunes et al. |
| 5,839,139 | A | 11/1998 | Fink |
| 5,848,979 | A | 12/1998 | Bonutti et al. |
| 5,865,773 | A | 2/1999 | Koledin |
| 5,882,320 | A | 3/1999 | Peterson |
| 5,882,323 | A | 3/1999 | Belkin |
| 5,919,148 | A | 7/1999 | Marko et al. |
| 5,929,782 | A | 7/1999 | Stark et al. |
| 5,940,992 | A | 8/1999 | Darby |
| 5,943,705 | A | 8/1999 | Sink |
| 5,951,499 | A | 9/1999 | Saringer et al. |
| 5,980,435 | A | 11/1999 | Joutras et al. |
| 6,007,500 | A | 12/1999 | Quintinskie, Jr. |
| 6,021,780 | A | 2/2000 | Darby |
| 6,027,468 | A | 2/2000 | Pick |
| 6,053,169 | A | 4/2000 | Hunt |
| 6,059,576 | A | 5/2000 | Brann |
| 6,076,266 | A | 6/2000 | Beckingham et al. |
| 6,093,162 | A | 7/2000 | Fairleigh et al. |
| 6,099,489 | A | 8/2000 | Herzberg et al. |
| 6,113,562 | A | 9/2000 | Bonutti et al. |
| 6,142,964 | A | 11/2000 | Gilmour |
| 6,142,965 | A | 11/2000 | Mathewson |
| 6,155,994 | A | 12/2000 | Hubbard et al. |
| 6,179,747 | B1 | 1/2001 | Kelley |
| 6,179,800 | B1 | 1/2001 | Torrens |
| 6,184,797 | B1 | 2/2001 | Stark et al. |
| 6,196,956 | B1 | 3/2001 | Brown |
| 6,228,044 | B1 | 5/2001 | Jensen et al. |
| 6,267,742 | B1 | 7/2001 | Krivosha et al. |
| 6,296,595 | B1 | 10/2001 | Stark et al. |
| 6,371,123 | B1 | 4/2002 | Stark et al. |
| 6,384,755 | B1 | 5/2002 | Hayden |
| 6,409,691 | B1 | 6/2002 | Dakin et al. |
| 6,436,058 | B1 | 8/2002 | Krahner et al. |
| 6,485,447 | B1 | 11/2002 | Lavery et al. |
| 6,491,694 | B1 | 12/2002 | Orsak |
| 6,502,577 | B1 | 1/2003 | Bonutti |
| 6,503,213 | B2 | 1/2003 | Bonutti |
| 6,506,172 | B1 | 1/2003 | Hepburn et al. |
| 6,509,659 | B1 | 1/2003 | Carroll et al. |
| 6,572,571 | B2 | 6/2003 | Lowe |
| 6,575,926 | B2 | 6/2003 | Bonutti |
| 6,599,255 | B2 | 7/2003 | Zhang |
| 6,599,263 | B1 | 7/2003 | Bonutti et al. |
| 6,637,429 | B2 | 10/2003 | Mundrick et al. |
| 6,682,497 | B2 | 1/2004 | Jensen et al. |
| 6,743,187 | B2 | 6/2004 | Solomon |
| 6,770,047 | B2 | 8/2004 | Bonutti |
| 6,890,285 | B2 | 5/2005 | Rahman et al. |
| 6,921,377 | B2 | 7/2005 | Bonutti |
| 6,929,616 | B2 | 8/2005 | Bonutti et al. |
| 6,958,048 | B2 | 10/2005 | Bonutti |
| 6,974,431 | B2 | 12/2005 | Jensen |
| 7,101,347 | B2 | 9/2006 | Culhane et al. |
| 7,112,179 | B2 | 9/2006 | Bonutti et al. |
| 7,182,738 | B2 | 2/2007 | Bonutti et al. |
| 7,204,814 | B2 | 4/2007 | Zalman |
| 7,306,573 | B2 | 12/2007 | Bonutti |
| 7,404,804 | B2 | 7/2008 | Bonutti |
| 2001/0047209 | A1 | 11/2001 | Solomon |
| 2002/0029784 | A1 | 3/2002 | Stark |
| 2002/0183655 | A1 | 12/2002 | Zhang |
| 2004/0153010 | A1 | 8/2004 | Bonutti |
| 2004/0215120 | A1 | 10/2004 | Jensen |
| 2005/0197605 | A1 | 9/2005 | Bonutti |
| 2006/0036205 | A1 | 2/2006 | Bonutti |
| 2007/0038161 | A1 | 2/2007 | Bonutti et al. |
| 2007/0055190 | A1 | 3/2007 | Bonutti et al. |
| 2007/0100267 | A1 | 5/2007 | Bonutti et al. |
| 2007/0135738 | A1 | 6/2007 | Bonutti et al. |
| 2007/0197605 | A1 | 8/2007 | Glombik et al. |
| 2007/0219475 | A1 | 9/2007 | Bonutti et al. |
| 2007/0219476 | A1 | 9/2007 | Bonutti et al. |
| 2008/0091132 | A1 | 4/2008 | Bonutti |

FOREIGN PATENT DOCUMENTS

| | | |
|---|---|---|
| CA | 2065669 | 10/1993 |
| DE | 405327 | 10/1924 |
| DE | 2829562 | 1/1980 |
| DE | 8806231.7 | 5/1988 |
| EP | 0181668 | 5/1986 |
| EP | 0181688 | 5/1986 |
| EP | 0380060 | 1/1990 |
| EP | 0510840 | 10/1992 |
| FR | 2661333 | 4/1990 |
| JP | 4261657 | 9/1992 |
| JP | 2001 087296 | 4/2001 |
| RU | 1426580 | 9/1988 |
| SU | 1158195 | 5/1985 |
| SU | 1671296 | 8/1991 |
| WO | WO 88/04543 | 6/1988 |
| WO | WO 2004/073143 | 1/2004 |
| WO | WO 2005/086741 | 9/2005 |
| WO | WO 2007/051168 | 5/2007 |
| WO | WO 2007/109638 | 9/2007 |
| WO | WO 2008/036895 | 8/2008 |

OTHER PUBLICATIONS

Advertising materials from the Internet on Jun. 5, 1998 entitled: “Quadrant by Smith & Nephew DonJoy” “Entering a New Plane”.

Advertising materials from the Internet on Jun. 5, 1998 entitled: “Make DonJoy’s Quadrant Your First Choice for Effective Post-Operative Shoulder Treatment”. “Quadrant Brace Specifications”.

Advertising materials from the Internet on Jun. 5, 1998 entitled: “Ultraslingtm by DonJoy”.

Neporent et al. “Weight Training for Dummies” 1997, p. 294.

Dynasplint Systems Inc., “Practitioner Information for Dynasplint LPS Orthosis—Knee Extension”, date known but prior to Aug. 23, 1991.

Publication by UE Tech, Technology Meeting Human Needs, Rehabilitation Product Catalog, vol. 7, publication date unknown, but prior to Oct. 13, 1998.

Taber’s Cyclopedic Medical Dictionary 16th Edition (1989) (#34), p. 521, definition of “distraction”.

Joint Active Sytems, Inc., JAS; The Proven Approach to Restoring ROM (online), Copyright 2004 www.jointactivesystems.com.

* cited by examiner

RANGE OF MOTION DEVICE

FIELD OF THE INVENTION

The present invention relates to an adjustable orthosis for stretching tissue in the human body. In particular, the present invention relates to an adjustable orthosis which can be used for stretching tissue such as ligaments, tendons or muscles around a joint during flexion or extension of the joint.

BACKGROUND OF THE INVENTION

In a joint, the range of motion depends upon the anatomy and condition of that joint and on the particular genetics of each individual. Many joints primarily move either in flexion or extension, although some joints also are capable of rotational movement in varying degrees. Flexion is to bend the joint and extension is to straighten the joint; however, in the orthopedic convention some joints only flex. Some joints, such as the knee, may exhibit a slight internal or external rotation during flexion or extension.

Most people do not appreciate the complexity of joint motion until something goes wrong, such as when an injury results in lost range of motion. When a joint is injured, either by trauma or by surgery, scar tissue can form or tissue can contract and consequently limit the range of motion of the joint. For example, adhesions can form between tissues and the muscle can contract itself with permanent muscle contracture or tissue hypertrophy such as capsular tissue or skin tissue. Lost range of motion may also result from trauma such as exposure to extreme temperatures, chemical burns, or surgical trauma so that tissue planes which normally glide across each other may become adhered together to markedly restrict motion. The adhered tissues may result from chemical bonds, tissue hypertrophy, proteins such as Actin or Myosin in the tissue, or simply from bleeding and immobilization. It is often possible to mediate, and possibly even correct this condition by use of a range-of-motion (ROM) orthosis, but the longer the period of stiffness or loss of motion the greater the time interval and the force required to regain lost range of motion. Therefore, it is beneficial to treat the tissue or joint as early as possible. For example, a ROM orthosis may be applied immediately after surgery or as soon as the stiffness problem is diagnosed.

ROM orthoses are devices commonly used during physical rehabilitative therapy to increase the range-of-motion over which the patient can flex or extend the joint. Commercially available ROM orthoses are typically attached on opposite members of the joint and apply a torque to rotate the joint in opposition to the contraction. The force is gradually increased to increase the working range or angle of joint motion. Exemplary orthoses include U.S. Pat. Nos. 6,921,377 ("Finger Orthosis"), 6,770,047 ("Method of using a neck brace"), 6,599,263 ("Shoulder Orthosis"), 6,113,562 ("Shoulder Orthosis"), 6,503,213 ("Method of using a neck brace"), 6,502,577 ("Finger Orthosis"), 5,848,979 ("Orthosis"), 5,685,830 ("Adjustable Orthosis Having One-Piece Connector Section for Flexing"), 5,611,764 ("Method of Increasing Range of Motion"), 5,503,619 ("Orthosis for Bending Wrists"), 5,456,268 ("Adjustable Orthosis"), 5,453,075 ("Orthosis with Distraction through Range of Motion"), 5,395,303 ("Orthosis with Distraction through Range of Motion"), 5,365,947 ("Adjustable Orthosis"), 5,285,773 ("Orthosis with Distraction through Range of Motion"), 5,213,095 ("Orthosis with Joint Distraction"), and 5,167,612 ("Adjustable Orthosis"), and U.S. Publication No. 20040215111 ("Patient monitoring apparatus and method for orthosis and other devices"), all to Bonutti and herein are expressly incorporated by reference in their entirety.

In the past, many ROM orthothes required manual operation, may not have been capable of accurately simulating the natural range of motion of a healthy joint, or may not have allowed for easy adjustment of the treatment protocol (e.g., force applied, range of motion exercised, duration of treatment, etc.).

SUMMARY OF THE INVENTION

The present invention provides an orthosis for stretching tissue around a joint of a patient by causing the joint to flex or move through a range of motion. In some cases, the range of motion through which the joint is moved is predetermined and well controlled. That is, the range of motion a joint experiences as it moves through one cycle of movement may be substantially the same as the range of motion that the joint travels through in a second cycle of movement during a treatment session. The range of motion through which the joint is exercised may be accomplished through flexion or extension of the joint, or through combinations of both flexion and extension.

Alternatively, the range of motion may be predetermined and well controlled by being capable of duplicating or at least approximating the range of movement a joint experiences in a treatment session, even if the range of motion varies between individual cycles of motion during a session. For example, the range of motion a joint experiences may vary in a predetermined and well controlled manner under this invention by gradually increasing or decreasing the range of motion the joint passes through over time, or by introducing motion in a different plane or direction, such as by combining flexing or bending movement with rotational movement, such as with an ankle, knee, elbow, or shoulder joint. Thus, even if there are some variations of range of motion in a treatment session, it may still be carried out in a predetermined and well controlled manner if a physician, technician, or patient could perform a second treatment session that was so similar to the first to be considered a repeated treatment session.

In some cases, the invention may be configured such that the range of motion through which the joint moves during a treatment session may be controlled to some extent, but not predetermined. For instance, while one or more components of a device operating according to this aspect of the invention may travel through a predetermined path, other components may be designed to allow for flexibility of the overall system in response to joint stiffness, limited range of motion, adhesions, or other patient-related factors. This may happen, for instance, if cushioning or flexibility is provided in the invention to account for differences in joint flexibility over time or between patients. Thus, while the settings of the device may be established to recreate substantially the same underlying movement of some component parts, changes in the treated joint over time may mean that the range of motion through which it moves may change.

For example, a patient fitted with a joint treatment apparatus according to the present invention is expected to gradually increase range of motion in the joint over time. Initially, however, the joint and surrounding tissue may not be capable of a wide range of motion without risking damage to the joint or surrounding tissue. To account for this, a force absorber or cushioning device may be used to limit the amount of force exerted on a joint, or at least reduce it to a lower level than may have been exerted if the device did not utilize a force absorber or cushioning device. As the resistive forces in the joint and surrounding tissue reach a threshold amount, the force absorber or cushioning device may bend, deflect, compress, or otherwise absorb some of this energy. As flexibility in the joint and surrounding tissue increases, operation of the force absorber or cushioning device will decrease and the range of motion the joint travels through will increase.

In one embodiment of the invention, the orthosis includes a first member affixable to a first body portion, such as a foot of a user. The first member has a first extension member extending therefrom. A second member affixable to the second body portion, such as on at least one toe on the foot is also included. The second member includes a second extension member having an arcuate shape extending therefrom. The second and first members are operatively connected, such that the second extension member travels through the first extension member along an arcuate path when the second member is moved from a first position to a second position relative to the first member.

The range of motion generated by an orthosis of the present invention may be created or carried out in several ways. In the embodiment described above, for instance, a portion of the device follows an arcuate path. For purposes of the present invention, the term arcuate path is to be interpreted broadly to include, for example, known or defined geometric paths, such as all or part of an arc of a circle, ellipse, oval, parabola, or other mathematically definable curves or portions of geometrically defined curved shapes. Relative movement of component parts of an orthosis of the present invention may utilize cams and followers, inter-connecting gears, or other structures or systems to cause the joint to move at least partially through a desired range of motion. As explained in greater detail below, however, some alternative embodiments described below may utilize one or more components moving in a linear or even in an angular direction. Additionally, two or more components may be moveable such that the net effect of these movements results in forces being exerted on the joint generally in the direction of the natural movement of the joint.

In some embodiments, the orthosis may also have a drive assembly that provides for continuous, cyclic operation of the orthosis through ranges of motion over time. The length of time or number of cycles that the orthosis exercises the range of motion of the joint may be varied according to a desired treatment protocol, patient comfort, or other factors. Likewise, the amount of movement or force exerted on the joint may be varied during operation of the drive assembly. The drive assembly may be mounted onto the first extension member, thereby engaging the second extension member. The drive assembly can be manually or automatically actuated to selectively move the second extension member relative to the first extension member.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention relates to an orthosis for causing a joint to flex or move through a range of motion. One exemplary application of an orthosis of the present invention is in treatment of a toe of a patient's foot. While the invention is believed to provide significant improvements in this area of treatment, it may likewise be of benefit in treating other joints, such as ankles, knees, hips, fingers, wrists, elbows, shoulders, or the spine.

Furthermore, while many examples provided herein may illustrate the invention used to treat the metatarsal and proximal phalanx of the toe, these examples are non-limiting on other joints of the toe that also may be treated by the present invention. It is understood by those skilled in the art that the other joints of the toe may be flexed or extended, without departing from the spirit and scope of the invention. Additionally, the present invention is described in use on the "big" toe or hallux on the foot. Thus, it should be understood by those skilled in the art that the present invention is equally applicable for use on the second, third, fourth and minimus toes of the foot.

Each toe in the foot extends from the metatarsal bone and is formed by the proximal phalanx, middle phalanx, and distal phalanx, each of which is respectively pivotally connected to form a joint there between. The orthosis of the present invention may be configured to flex or extend (or both) a toe joint, where the joint defines an inner sector on the flexor side that decreases in angle as the joint is flexed (bent) and an outer sector on the extensor side that decreases in angle as the joint is extended (straightened).

Figure 1:
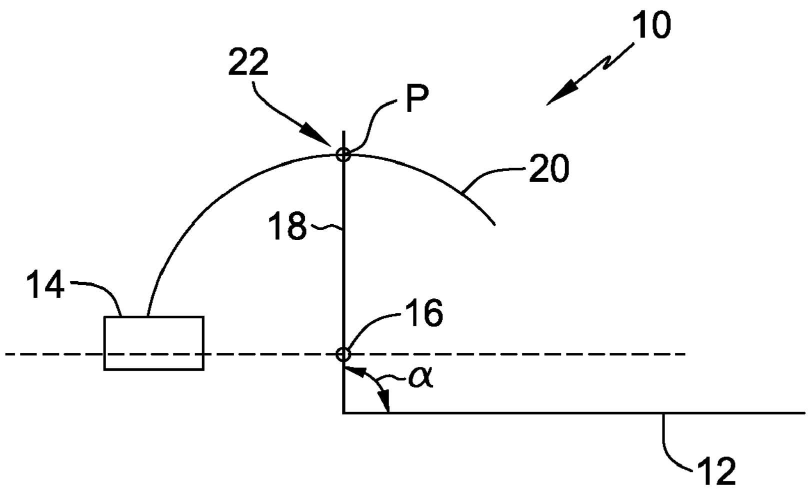
FIG. 1 is a schematic diagram of an orthosis of the present invention.

Referring now to the figures in which like reference designators refer to like elements, there is shown in FIG. 1, a schematic of the orthosis 10 of the present invention. The orthosis 10 includes a first member 12 attachable to a first body portion, such as a user's foot. The shape and configuration of the first member 12 may be selected to support or conform generally to a patient's foot. For example, the first member 12 may be a platform that contacts or supports the underside of a user's foot. Sidewalls or curved edges may be provided to help position, cradle, or securely hold the foot in proper position.

Alternatively, the first member 12 may have a profile or shape that generally conforms to a user's arch, shoe size, or foot width so that it fits more comfortably, holds the foot securely in place, or improves alignment of the device so that the range of motion imparted by the device corresponds to a joint's healthy range of motion. This conforming shape or profile may be accomplished, for instance, by providing interchangeable platforms corresponding to different foot sizes and shapes. The interchangeable platform may be selectively removed and replaced by an interchangeable platform of a different size. Alternatively, the first member 12 may have adjustable surfaces that can be resized or repositioned to better support or correspond to a patient's foot. For example, the overall length of the first member 12 may be adjustable, or the width of the first member 12 near the toes may be adjusted to account for different foot widths. In addition, raised walls or edges that support the feet may be selectively moveable so that they can be moved to accommodate different foot sizes. Once the foot is in place and the edges are moved to their desired position, they may be selectively locked or secured in place to help hold the foot in place. Additionally, the first member 12 may be configured with an arch, which in some instances also may be adjustable such as by having interchangeable arch inserts, by configuring the arch to be inflatable, or the like.

The first member 12 is operatively associated with or connected to a second member 14 so that the first and second members 12 and 14 may move or rotate with respect to each other. As shown in FIG. 1, the supporting surface of the first member 12 may be offset from the supporting surface of the second member 14. This amount of offset provided may vary from patient to patient or from joint to joint, and in some cases an offset may not be provided. Thus, it may be advantageous to allow the offset of the orthosis 10 to be adjustable so that a physician or user may change its size as needed to improve comfort, fit, or operation of the orthosis 10.

Figure 2:
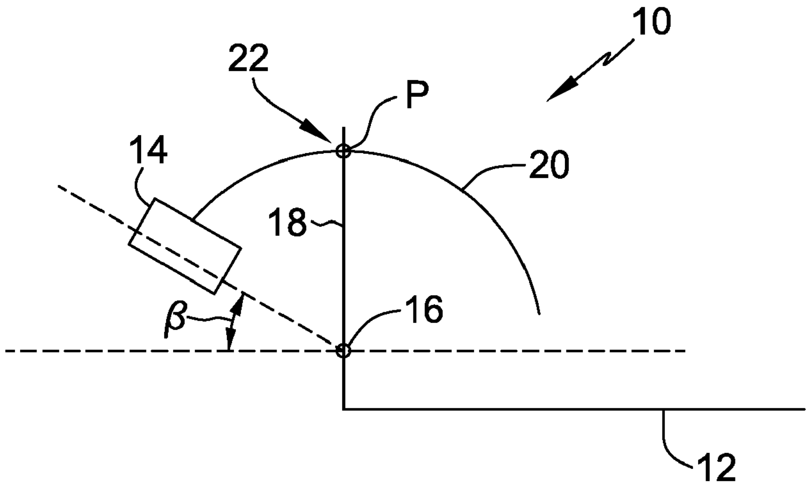
FIG. 2 is a schematic diagram of the orthosis of FIG. 1 in an extended position.
Figure 3:
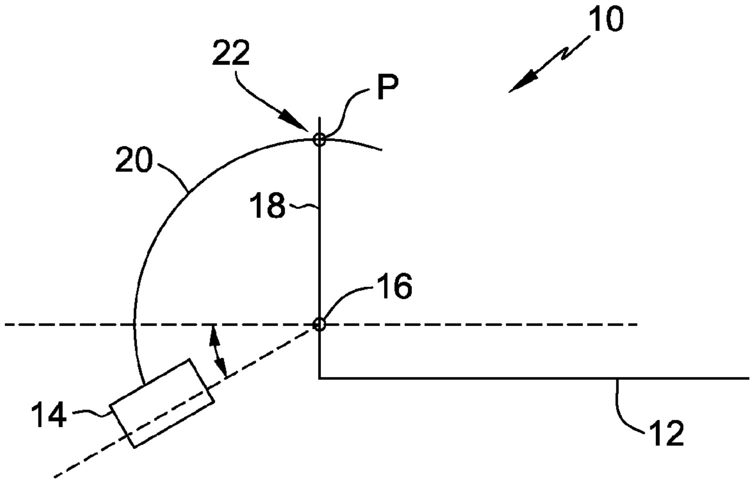
FIG. 3 is a schematic diagram of the orthosis of FIG. 1 in a flexed position.

In use, the second member 14 may be attachable to a second body portion, such as at least one toe on the foot so that the relative movement of the two members also causes movement of the joint. As shown in FIG. 1, the orthosis 10 may have an axis of rotation 16 that is aligned with the axis of rotation of the joint. In this manner, the instantaneous axis of rotation (TAR) of the first and second members 12 and 14 may better match the IAR of the treated joint. As will be discussed in greater detail below, while the axis of rotation 16 of the device is illustrated in FIGS. 1-3 as occurring only along a single line, the axis of rotation 16 may also shift or move depending on the relative positioning of the first and second members 12 and 14 in a manner that corresponds to changing axis of rotation that a joint may experience through its range of motion. The first and second members 12 and 14 are operatively connected to each other, offset from the orthosis axis 16.

The first member 12 of the orthosis 10 includes a first extension member 18 extending therefrom. The second member 14 of the orthosis 10 includes a second extension member 20 extending thereform and having an arcuate shape. The first and second extension members 18 and 20 are operatively connected at point "P," such that in operation the second extension member 20 travels along an arcuate path about and substantially through point "P." The arcuate shape of the second extension member 20 results in the toe rotating about the orthosis axis 16, or alternatively about a moving IAR, when the second member 14 is moved from a first position to a second position relative to the first member 12.

The first extension member 18 can extend substantially vertically from the first member 12 or extend at an angle α from the first member 12. In one embodiment of the invention, the angle α and the radius of curvature of the second extension member 20 are configured such that of the orthosis axis 16 is aligned with the axis of rotation of the joint.

The previous description of the first member 12 depicts a first extension 18 having a substantially linear shape, extending at an angle α from the first member 12. However, it is within the scope of the present invention that the first extension member 18 can be any shape extending from the first member 12 which aligns orthosis axis 16 with the axis of rotation of the joint. Furthermore, as mentioned previously and again below, in some instances the axis of rotation of the joint may change or move slightly. Therefore, in some instances it may be desirable for the orthosis to mimic the IAR of the joint. As will be illustrated in detail below, this can be accomplished in several ways. One modification of the embodiment of the invention shown in FIG. 1, for instance, may be for the second extension member 20 not to have a constant radius of curvature.

The orthosis 10 further includes a drive assembly 22, which is illustrated in FIG. 1 at or near point "P." In this embodiment, the drive assembly 22 is operably connected to the first and second extension members 18 and 20 for applying force to the first and second members 12 and 14 to pivot the second body portion about the orthosis axis 16. As will be shown below in additional embodiments, the drive assembly 22 may be configured or disposed to interact with or operate on one of the first or second members 12 and 14 independently.

Referring to FIG. 2, in order for the orthosis 10 to extend the joint the first and second members 12 and 14 may be affixed to the first and second body portions, respectively, tightly enough so that the first and second members 12 and 14 can apply torque to extend the joint. The second extension member 20 is moved through the drive assembly 22 from a first position to a second position, relative to the first extension member 18, rotating the second member 14 and the second body portion about the orthosis axis 16 stretching the joint. As the second member 14 is rotated to the second position, the second extension member 20 travels at least partially through point "P" and may travel substantially through this point for a large range of motion. Because the first and second members 12 and 14 are affixed to the first and second body portions, the outward pivoting movement of the second member 14 causes the joint to be extended as desired. The orthosis 10 may then be maintained in the second position for a predetermined treatment time providing a constant stretch to the joint. The orthosis may alternatively be configured to impart a constant force or load on the joint or may utilize the techniques of Static Progressive Stretch as described in co-pending application Ser. No. 11/203,516, entitled "Range of Motion System and Method", and filed on Aug. 12, 2005, the entirety of which is incorporated by reference.

Returning to the example where the orthosis is maintained in the second position, after the expiration of the treatment time, the second member 14 may then be moved back to the first position, relieving the joint. Optionally, the second member 14 can be rotated to a third position, increasing the stretch on the joint, or partially reducing it to allow limited relaxation of the surrounding tissue. The second member 14 can be rotated at discrete time intervals to incrementally increase, reduce, or vary the stretch of the joint through the treatment cycle. After completion of the treatment cycle, the second arm 14 is returned to the first position for removal of the orthosis 10.

Referring to FIG. 3, in operation of the orthosis 10 to flex the joint. The first and second members 12 and 14 are affixed to the first and second body portions, respectively, tightly enough so that the first and second members 12 and 14 can apply torque to extend the joint. A cuff, strap, laces, or other retaining device may be used to securely associate respective body portions of the joint with the first and second members 12, 14. The second extension member 20 is moved through the drive assembly 22 from the first position to a second position, relative to the first extension member 18, rotating the second member 14 and the second body portion about the orthosis axis 16 stretching the joint. As the second member 14 is rotated to the second position, the second extension member 20 travels substantially through point "P." Because the first and second members 12 and 14 are affixed to the first and second body portions, the inward pivoting movement of the second member 14 causes the joint to be flexed as desired. The orthosis 10 is maintained in the second position for a predetermined treatment time providing a constant stretch to the joint.

After the expiration of the treatment time, the second member 14 is moved back to the first position, relieving the joint. Optionally, the second member 14 can be rotated to a third position, thereby increasing, decreasing, or otherwise varying the stretch on the joint. The second member 14 can be rotated at discrete time intervals to incrementally increase the stretch of the joint through the treatment cycle. After completion of the treatment cycle, the second arm 14 is returned to the first position for removal of the orthosis 10.

Figure 4:
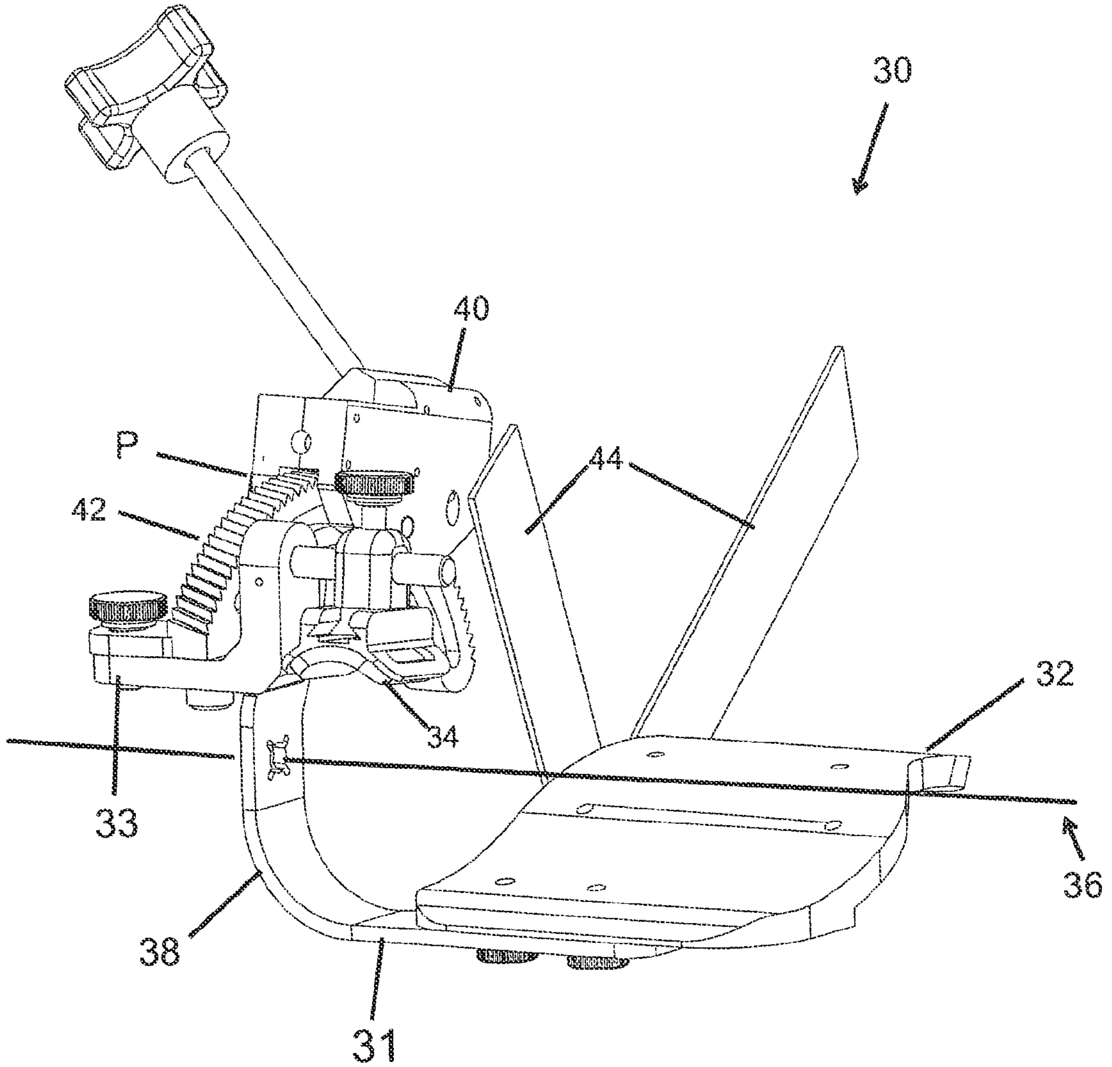
FIG. 4 is an isometric view of an orthosis of the present invention.
Figure 5:
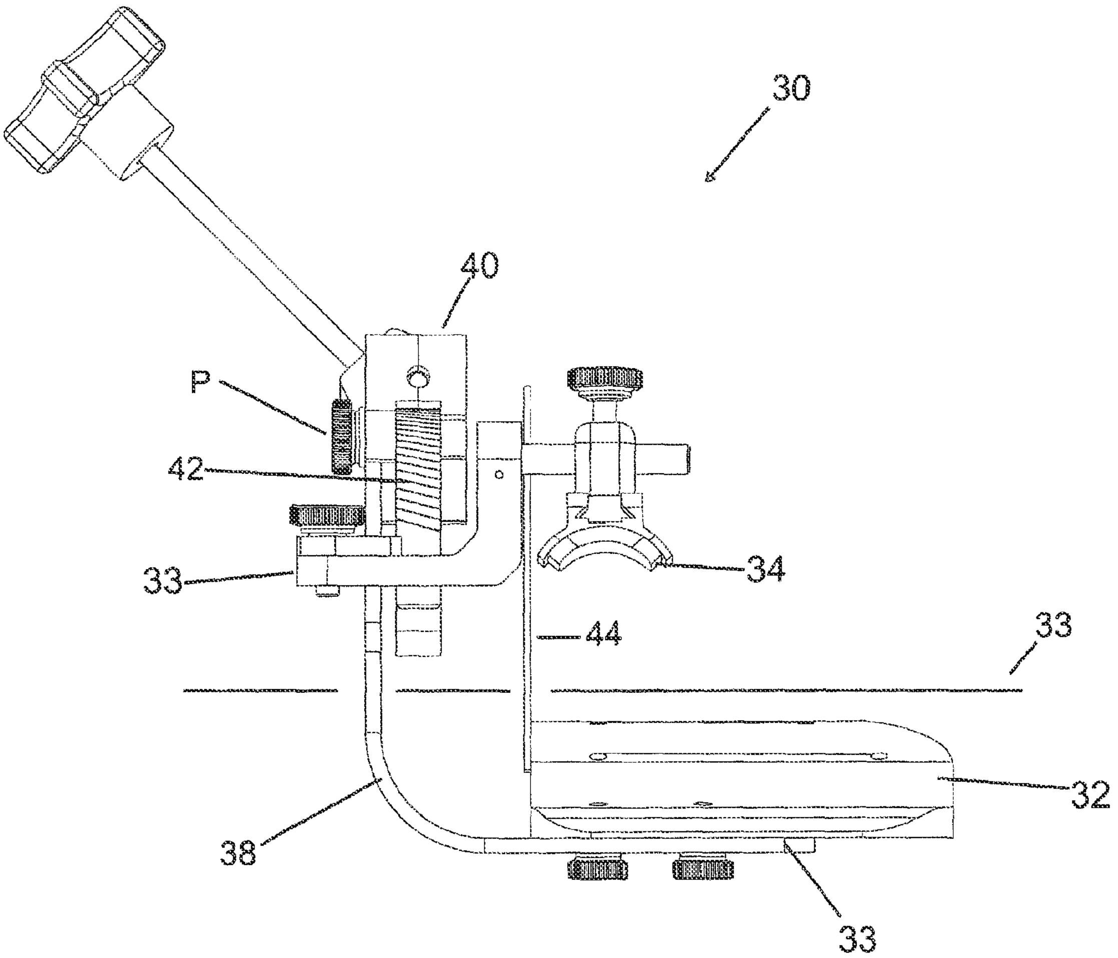
FIG. 5 is a front view of the orthosis of FIG. 4.
Figure 6:
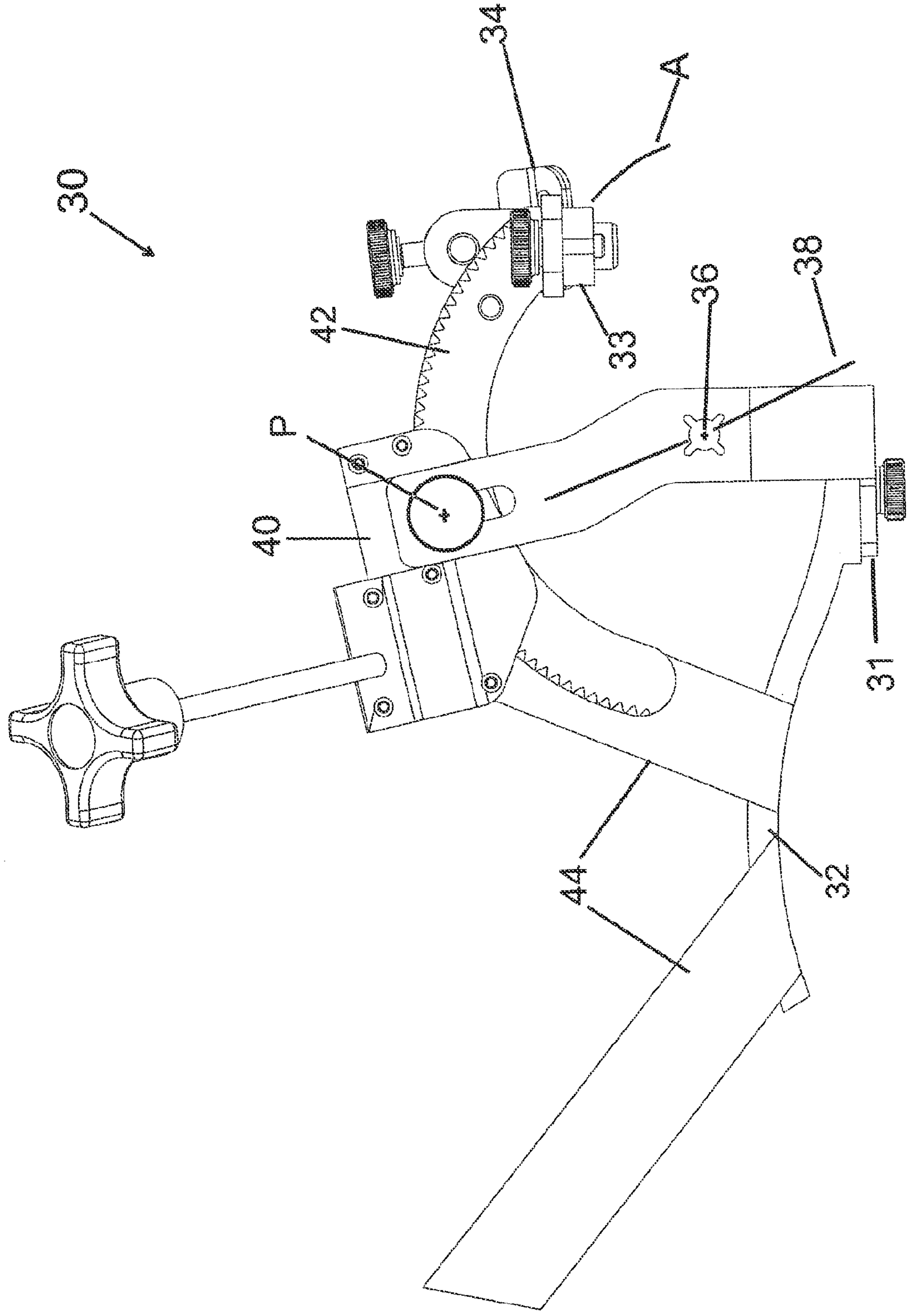
FIG. 6 is a side view of the orthosis of FIG. 4.

FIGS. 4-6 further illustrate several aspects of the invention more concretely. An orthosis 30 of the present invention includes a first member 31 having a first cuff 32 attachable to a user's foot and a second member 33 having a second cuff 34 attachable to a toe of the user's foot, wherein the second member 33 is rotatable with respect to the first member 31 about an axis of rotation 36. The first and second members 31 and 33 are attached to the foot and toe of the user with the first and second cuffs 32 and 34, such that as the second member 33 is rotated about the axis of rotation 36, the toe is rotated about a joint axis.

A first extension member 38 is affixed to and extends from the first member 31, wherein a drive assembly 40 is positioned on an end portion of the first extension member 38. A second extension member 42 is similarly affixed to and extends from the second member 33, wherein the second extension member 42 has an arcuate shape. The second extension member 42 engages the drive assembly 40 of the first extension member 38 at a point "P." An actuation of the drive assembly 40 operates to move the second extension member 42 through the drive assembly 40, such that the second cuff 34 travels along an arcuate path "A" with respect to the first member 31. The arcuate shape of the second extension member 42 results in the toe rotating about the joint axis, as the second cuff 34 is moved along the arcuate path "A." The drive assembly 40 can be actuated to move the second cuff 34 and toe from a first position to a second position relative to the first cuff 32. Once again, the term "cuff" as used herein means any suitable structure for transmitting the force of the orthosis 30 to the limb portion it engages.

The first extension member 38 can extend substantially vertically from the first member 31 or extend at an angle $\alpha$ from the first member 31, where the angle $\alpha$ and the radius of curvature of the second extension member 42 (if constant) can be configured such that of the axis of rotation 36 is aligned with the joint axis of ration. As previously discussed, the curvature of the second extension member 42 need not be constant, and therefore the axis of rotation may shift or move in a manner that preferably mimics or approximates the moving IAR the joint would normally have. Another potential benefit of the orthosis 30 having the capability of a moving IAR is when multiple joints are being treated by the device. For instance, the range of motion of the tip of a toe or finger may involve cooperative motion of two or more joints. If the combined bending of the multiple joints causes the overall motion to rotation about a moving axis, it would be beneficial for the orthosis to approximate this moving IAR. Thus, the curvature of the second extension member 42 may be complex in order to better approximate a moving IAR.

Figure 7:
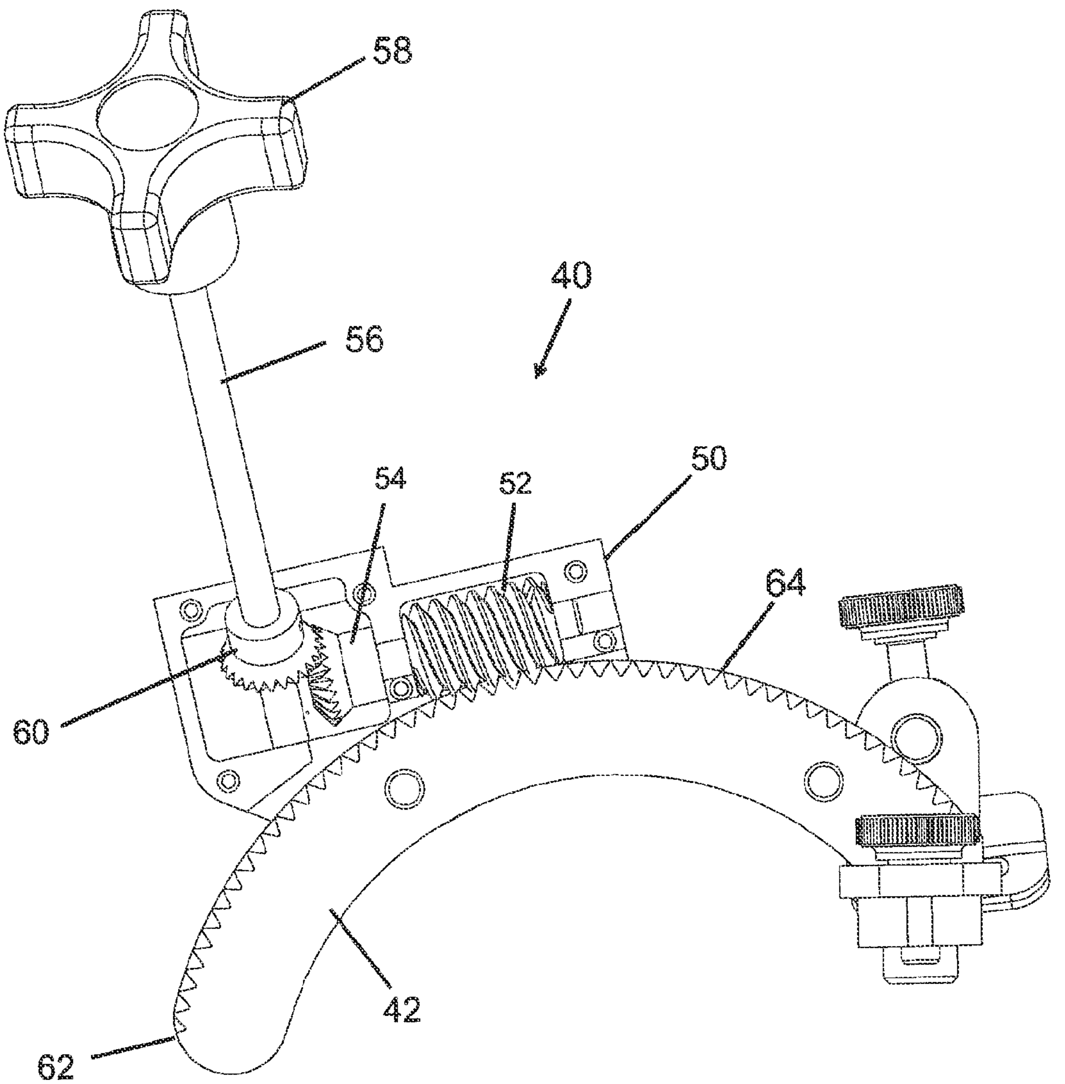
FIG. 7 is a sectional view of a drive assembly of the orthosis of FIG. 4.

Referring to FIG. 7, the drive assembly 40 can include a housing 50 having a worm gear 52 therein. A first miter gear 54 is attached to the worm gear 52 such that a rotation of the first miter gear 54 rotates the worm gear 52. The drive assembly 40 further includes a drive shaft 56 have a knob 58 at one end and a second miter gear 60 at an opposite end. The second miter gear 60 is positioned within the housing 50, in engagement with the first miter gear 54. A rotation of the knob 58 rotates the drive shaft 56 and the second miter gear 60, which in turn rotates the first miter gear 54 and the worm gear 52.

A gear surface 62 of the second extension member 42 includes a plurality of teeth 64. The second extension member 42 is positioned throughout the housing 50, such that the worm gear 52 engages the teeth 64 of the second extension member 42. A rotation of the knob 58 rotates the worm gear 52, which in turn moves the second extension member 42 through the housing 50.

In an alternative embodiment, the drive assembly 40 for orthosis 30 in accordance with the present invention can be actuated by a motor instead of by a manually actuatable member, such as the knob 58. Likewise, the motor may be configured an adapted with gearing that causes the orthosis to cycle through a range of motion in a predetermined manner, or alternatively maybe controlled by a programmable logic controller (PLC).

In an embodiment, an electric motor is mounted to the drive shaft 56 for rotation of the second miter gear 60. A battery or other source of energy provides electric power to the motor. Alternatively, the motor can be supplied with external power. A microprocessor controls the operation of the motor. The microprocessor and motor together can be used to cycle the second cuff 34 through a plurality of positions that cause the joint to undergo a range of motion, either by extension, by flexion, or both. For example, the microprocessor may be used to move the second cuff 34 in one pivotal direction a certain amount, hold there while tissue stretches, then move further in that direction; or in any other manner.

In another manner of use, the orthosis can be set to cycle to one end of the joint's range of motion and hold there for a predetermined period of time, then cycle to the other end of the joint's range of motion and hold there. The programming and control of the microprocessor is within the skill of the art as it relates to driving the motor to control the second cuff 34 to move in known manners. This embodiment is ideally suited for continuous passive motion exercise, because the orthosis is portable and because the motor can be programmed with the desired sequence of movements.

It should be understood that the particular physical arrangement of the motor, the power source, and the microprocessor is not the only possible arrangement of those elements. The invention contemplates that other arrangements of these or similarly functional elements are quite suitable, and thus, the invention is intended to cover any such arrangement.

Additionally, another type of power source, other than an electric motor, can also be used. For example, the use of a hydraulic or pneumatic motor as the drive mechanism is contemplated.

The present invention can further include a monitor for use with the orthosis 30, which provides assurances the patient is properly using the orthosis 30 during his/her exercise period For instance, the monitor can have a position sensor, a temperature sensor, a force sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly.

This analysis may be conducted remotely, thereby saving the time and expense of a home visit by a healthcare professional or technician. An exemplary monitoring system is provided in U.S. Publication No. 20040215111 entitled "Patient Monitoring Apparatus and Method for Orthosis and Other Devices," to Bonutti et al., the content of which is herein expressly incorporated by reference in its entirety.

In an exemplary use, the orthosis 30 is operated to rotate a toe about a joint axis in the following manner. The first cuff 32 is fastened about the foot with one or more straps, laces, or similar retaining device. Similarly, the second cuff 34 is fastened securely to the toe of the user, such that the joint and joint axis 36 is interposed between the first and second cuffs 32 and 34. The orthosis 30 is attached to the foot and toe in a first position. The drive assembly 40 is actuated to move the second extension member 42, such that the second cuff 34 travels along an arcuate path from the first position to a second position, relative to the first cuff 32, rotating the toe about the joint axis stretching the joint. The orthosis 30 is maintained in the second position for a predetermined treatment time providing a constant stretch to the joint. After the expiration of the treatment time, the second cuff 34 is moved back to the first position, relieving the joint. Optionally, the second cuff 34 can be rotated to a third position, thereby increasing or decreasing the stretch on the joint. The second cuff 34 can be rotated at discrete time intervals to incrementally increase the stretch of the joint through the treatment cycle. After completion of the treatment cycle, the second arm member is returned to the first position for removal of the orthosis 30.

Figure 8:
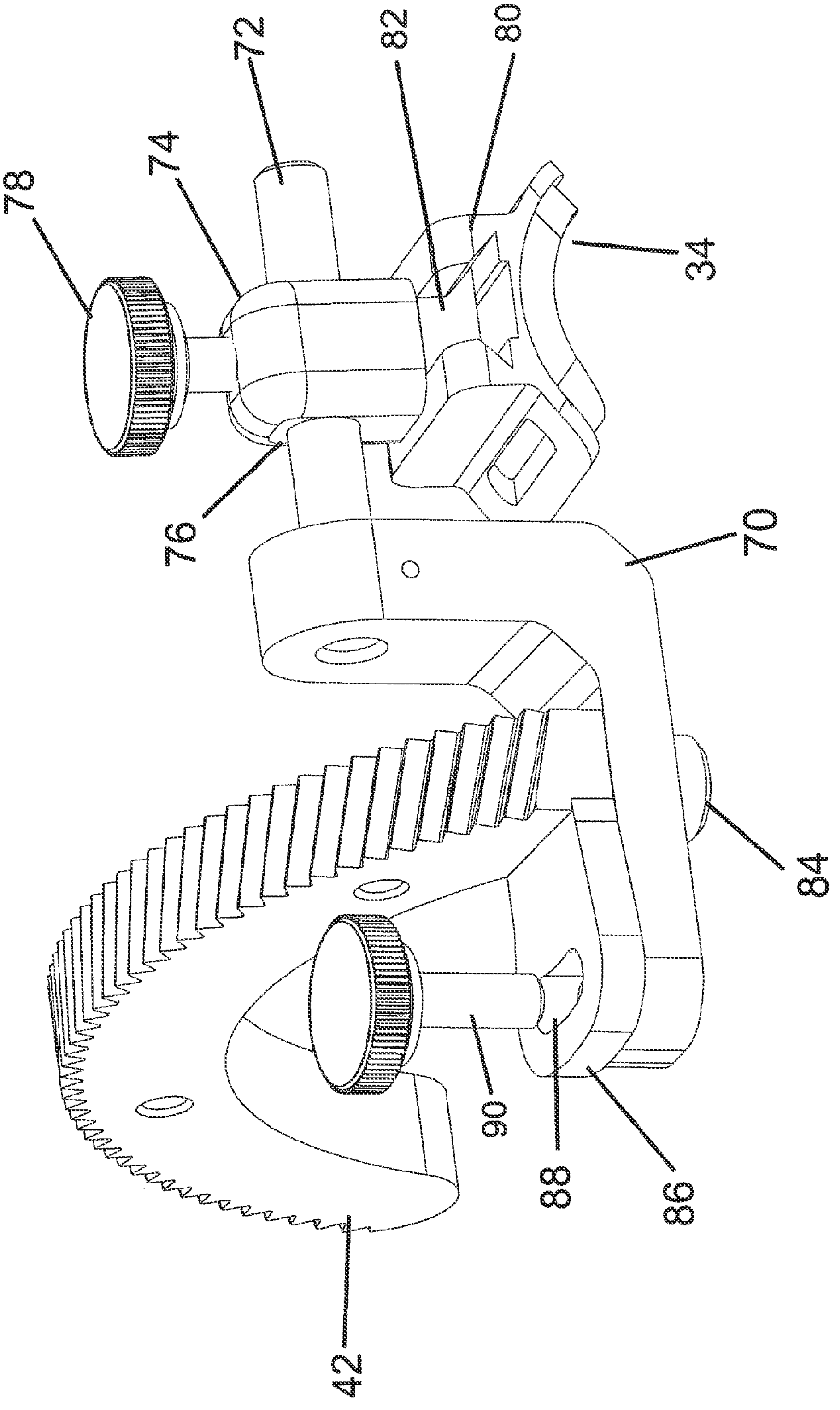
FIG. 8 is a section view of an adjustable second cuff for the orthosis of FIG. 4.

Referring to FIG. 8, the second member 33 can include an attachment bracket 70 for adjustably attaching the second cuff 34 to the second extension member 42. The attachment bracket 70 can include a toe rod 72 extending therefrom. The second cuff 34 can be slideably mounted on the toe rod 72 to position second cuff 34 over the toe. Alternatively, the toe rod 72 can be of sufficient length such that the second cuff 34 can be slidingly positioned on a selected toe on the foot of the user, for example, the big toe, minimus toe, or any toe therebetween.

The second cuff 34 can be positioned on the toe rod 72 with a first bracket 74, where the toe rod 72 passes through a passage 76 in the first bracket 74. A set screw 78 is provided to secure the first bracket 74 to the toe rod 72. When the set screw 78 is loosened, the first bracket 74 is free to slide along the toe rod 72. A tightening of the set screw 78 secures the first bracket 74 in place on the toe rod 72.

The second cuff 34 can further include a second bracket 80, where the second bracket 80 can be pivotally mounted to the first bracket 74. For example, the second bracket 80 can be attached to the first bracket 74 with a pin or screw connector, allowing the second bracket 80 to rotate with respect to the first bracket 74.

Additionally, when a joint is flexed or extended a compressive force may be applied to the connective tissue surrounding the joint. It may be desirable to control the compressive force, distracting the joint as the joint is flexed or extended. "Distraction" is defined by one dictionary as "Separation of the surfaces of a joint by extension without injury or dislocation of the parts." (Taber's Cyclopedic Medical Dictionary, 16th Edition, 1989, page 521), and involves stretching rather than compressing the joint capsule, soft tissue, ligaments, and tendons.

Additionally, the second bracket 80 can be slideably mounted to the first bracket 74. For example the second bracket 80 can be mounted to the first bracket 74 with a dovetail joint 82, allowing the second bracket 80 to slide with respect to the first bracket 74. The sliding movement of the second cuff 34 helps to limit the distractive or compressive forces which can be imparted on the joint by the rotation of the second cuff 34 with respect to the first cuff 32.

The attachment bracket 70 can be pivotally mounted to the second extension member 42. For example, the attachment bracket 70 can be attached to the second extension member 42 with a pin or screw connector 84, allowing the attachment bracket 70 to rotate with respect to the second extension member 42. The second extension member 42 further includes a extension bracket 86 having a slotted portion 88. A set screw 90 is positionable through the slotted portion 88, engaging the attachment bracket 70, such that the set screw 90 can be used to control the pivotal position of the attachment bracket 70 with respect to the second extension member 42.

The adjustable connection of the second cuff 34 to the attachment bracket 70 and the pivotal connection of the attachment bracket 70 to the second extension member 42 can be used to align the second cuff 34 with the toe. The alignment of the second cuff 34 on the toe can be used to substantially limit the force applied to the toe to that of a torque about the joint axis 36.

Bending a Joint in Extension:

In operation of the orthosis 30 to extend the joint, the orthosis starts at a more flexed position. The first and second cuffs 32 and 34 are clamped onto the foot and toe portions, respectively, by straps 44, tightly enough so that the first and second members 31 and 33 can apply torque to extend the joint. The second extension member 42 is moved through the drive assembly 40 from the first position to a second position, relative to the first extension member 38, rotating the second cuff 34 and the toe about the orthosis axis 36 stretching the joint. As the second cuff 34 is rotated to the second position the second extension member 42 travels along an arcuate path "A" about and substantially through point "P." The orthosis 30 is maintained in the second position for a predetermined treatment time providing a constant stretch to the joint.

As the orthosis 10 is rotated from the first position to the second position, extending the joint, the second cuff 34 moves along the first bracket 74. Because the first and second members 31 and 33 are clamped onto the foot and toe as described above, the outward pivoting movement of the second cuff 34 causes the joint to be extended as desired. However, this extension of the joint can place strong distractive forces on the soft tissues around the joint. The sliding movement of the second cuff 34 helps to limit these distractive forces by counteracting the outward movement. Thus, the detrimental effects of strong distractive forces normally generated in forced extension of a joint are avoided, being replaced with the beneficial effects of limited and controlled distraction.

Bending a Joint Flexion:

In operation of the orthosis 30 to flex the joint, the orthosis 30 starts at a more extended position. The first and second cuffs 32 and 34 are clamped onto the foot and toe portions, respectively, by straps 44, tightly enough so that the first and second members 31 and 33 can apply torque to extend the joint. The second extension member 42 is moved through the drive assembly 40 from the first position to a second position, relative to the first extension member 38, rotating the second cuff 34 and the toe about the orthosis axis 36 stretching the joint. As the second cuff 34 is rotated to the second position the second extension member 42 travels along an arcuate path "A" about and substantially through point "P." The orthosis 30 is maintained in the second position for a predetermined treatment time providing a constant stretch to the joint.

As the orthosis 30 is rotated from the first position to the second position, flexing the joint, the second cuff 34 moves along the first bracket 74. Because the first and second members 31 and 33 are clamped onto the foot and toe as described above, the inward pivoting movement of the second cuff 34 causes the joint to be flexed as desired. However, this flexion of the joint can place strong compressive forces on the soft tissues around the joint. The sliding movement of the second cuff 34 helps to limit these compressive forces by counteracting the inward movement. Thus, the detrimental effects of strong compressive forces normally generated in forced flexion of a joint are avoided, being replaced with the beneficial effects of limited and controlled compression.

While the embodiment discussed above utilize a second extension member having an arcuate shape to control movement of the second member relative to the first, it should be understood that skilled artisans having the benefit of this disclosure will appreciate that other configurations may likewise provide similar relative movement.

Figure 9:
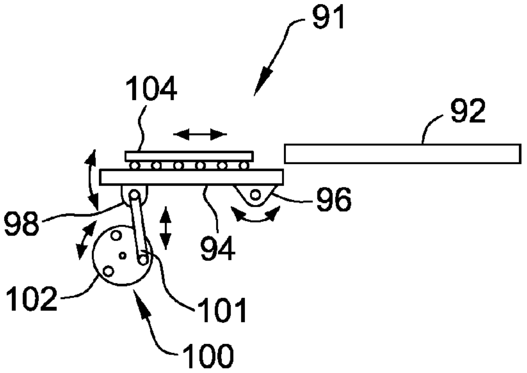
FIG. 9 is a schematic diagram of an embodiment of an orthosis of the present invention.
Figure 10:
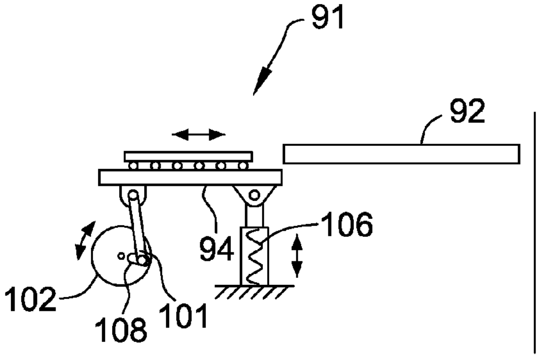
FIG. 10 illustrates another embodiment of the invention utilizing a cushion or spring.

FIG. 9, for example, schematically illustrates an embodiment of an orthosis 91 of the invention having a first member 92 and a second member 94, both of which preferably having sufficient structure or component parts to hold body members near the treated joint or joints. In the embodiment illustrated in FIG. 9 the second member has a first pivoting contact point 96 about which the geared body member may rotate. In this embodiment, the first pivoting contact 96 does not move in relation to the first body member 92, but as indicated in FIG. 10 one alternative embodiment may allow relative movement that can be resisted by a flexible device 106 such as a spring, compressed gas, foamed material, elastomer or the like.

Returning once again to FIG. 9, the second member may have an additional pivot contact 98, preferably disposed at a location at or near the opposite end of the second member 94 from where the first pivoting contact 96 is located. The second pivoting contact 98 may be configured with a drive assembly 100 that causes the second member 94 to follow a predetermined path. Thus, the second pivoting contact 98 in the embodiment of FIG. 9 is configured to move relative to the first member 92 in order to cause the joint to move from a first position to second one.

The drive assembly 100 illustrated in FIG. 9 is an arm or linkage 101 connected between the second pivot connection 98 and a rotating wheel 102. The wheel 102 may be configured so that the linkage 101 can be selectively connected to it in different radial distances from the center of rotation of the wheel. This allows the range of motion to be adjustable by the care provider, physician, or patient. As the wheel 102 is rotated, the linkage 101 moves in a manner that causes the second member 94 to move in a particular way.

The second member 94 (or alternatively the first member 92) may also have a sliding contact surface 104. The sliding contact surface 104 allows the joint to rotate or move according to its natural instantaneous axis of rotation. Thus, if the second pivot contact 98 moves in a manner that does not always exactly correspond to the axis of rotation of the joint, the sliding contact surface 104 may move or adjust accordingly. Another potential advantage of the sliding contact surface 104 is that is may help facilitate proper alignment of the joint in the orthosis during initial setup.

FIG. 10 illustrates some variations that may also be used in orthosis of the invention. For instance, the first and or second pivot contact may be configured with a cushion or spring 106 that allows one or both ends of the second member to impart some flexibility in the force imparted to the joint. As noted above, the cushion or spring 106 may be made of a variety of suitable materials and constructions to permit some flexibility in the movement of the pivot points 96, 98.

The use of a spring or cushion allows the orthosis 91 to be used in different treatment protocols than just by holding the joint in a prescribed location for a period of time. Instead, the orthosis can utilize the principles of static progressive stretch as described in copending application Ser. No. 11/203,516, entitled "Range of Motion System and Method", and filed on Aug. 12, 2005, the entirety of which is incorporated by reference.

Thus, an orthosis 91 configured with a spring or cushion 106 can be moved from an initial position to a second position that is determined not by position of the joint but instead by the amount of force the orthosis 91 imparts on the joint. The joint may then be subjected to this loading, and over time as the surrounding tissue stretches the joint will move and the imparted forces will be reduced. It should be noted that while FIG. 10 illustrates the cushion or spring 106 associated with the first pivot contact 96, it is not required to be associated with it. Instead, for example, the cushion or spring 106 may be associated with the second pivot 98 so that it can flex or move in response to resistive forces of the joint and nearby tissue. Likewise, there may be a spring or cushion 106 associated with both pivot contacts 96, 98.

Another notable variation between the embodiments of FIGS. 9 and 10 is that the rotating wheel 102 in FIG. 9 has multiple single point connections for connecting the linkage 101 at different distances from the center of rotation of the wheel. In contrast, the embodiment of FIG. 10 illustrates that an elongated slot 108 may be used to connect the linkage 101. The advantage of utilizing multiple single point connections may be ease of use and the ability to quickly confirm the orthosis 91 is properly configured for a prescribed treatment protocol, whereas one potential advantage of utilizing an elongated slot 108 is the ability to quickly adjust the settings without disassembling the device.

Figure 11:
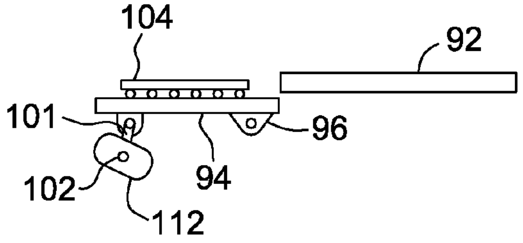
FIG. 11 is an embodiment of the invention illustrating the use of a cam surface.

FIG. 11 illustrates an embodiment of the invention where the rotating wheel 102 is a cam surface 112. This embodiment is similar to the use of cams and followers as described in U.S. Pat. No. 5,514,143, which is incorporated herein in its entirety. As shown, the cam surface 112 may have varying distance from the center or rotation of the wheel 102. If the wheel 102 is circular, for example, the center of rotation may be located somewhere different from the geometric center of the circle or at the center or rotation of the shape. As it rotates, the circumferential outer surface causes the linkage 101 to move to the second member 98 in a desired manner. Additionally, the outer edge of the "wheel" 102 need not be round, but instead may be a cam surface 112 of varying distance from the center or rotation. Likewise, the outer surface may have varying radii of curvature as shown in FIG. 11.

Figure 12:
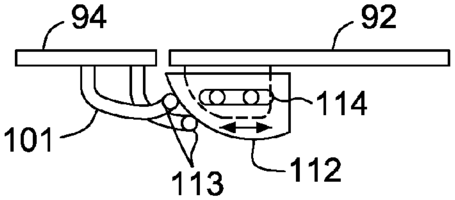
FIG. 12 is an embodiment of the invention utilizing a slideable arcuate surface.
Figure 13:
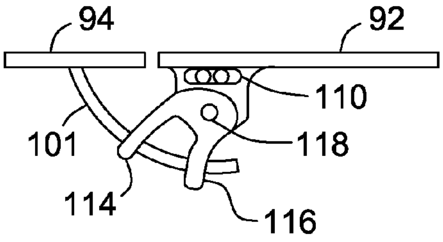
FIG. 13 illustrates features of an orthosis of the invention where the relative positions of component parts of the orthosis are adjustable.

The embodiments of FIGS. 12 and 13 further illustrate that a cam surface 112 may be used to move the second member 92 in a desired, perhaps complex way. As is the case for other embodiments described herein, performance of the cam surface 112 may be enhanced because of the ability to better mimic or replicate a moving axis of rotation of the treated tissue and joint.

In FIG. 12, the cam surface 112 is associated with the first member 92. Linkages or arms 101 of the second member 94 have cam followers 113 that trace the cam surface 112 and cause the second member 94 to move in a more complex manner than just by rotation around a fixed axis.

The cam surface 112 of FIG. 12 also is associated with a slot 100 that allows the relative location of the first and second members 92 and 94 to be adjusted or moved without decoupling the cam followers 113 from the cam surface 112. As shown, the slot 110 allows for horizontal adjustment repositioning. Although not shown, vertical slots may also be provided, either alone or in combination with a horizontal slot.

FIG. 13 illustrates an example where the linkage 100 is a cam surface 112 that passes through two or more points 114, 116 that are stationary or fixed relative to the first member 92 when the orthosis 91 is in use (i.e. after alignment is completed). Once again, this embodiment may be configured to permit horizontal adjustment, such as by providing slot 110, and likewise may be configured to be vertically adjustable. In addition, this embodiment also illustrates that the first and second members 92 and 94 may be represented by rotation about a pivot 118. Thus, the use of horizontal, vertical, and rotational adjustment of the relative positions of the first and second members 92 and 94 may allow greater fitting of the orthosis 91 to the treated tissue and joint.

Figure 14:
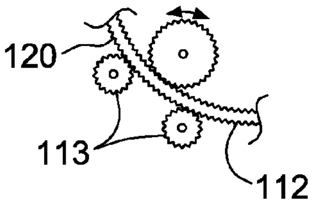
FIG. 14 is an illustration of the use of gears with an arcuate or cam surface of an orthosis of the invention.

FIG. 14 is an exploded view of how the cam surface 112 and cam followers 113 may utilize a geared surface 120. Utilizing a geared surface 120 may allow for a drive assembly 100 to automate the movement of the orthosis 91.

Figure 15:
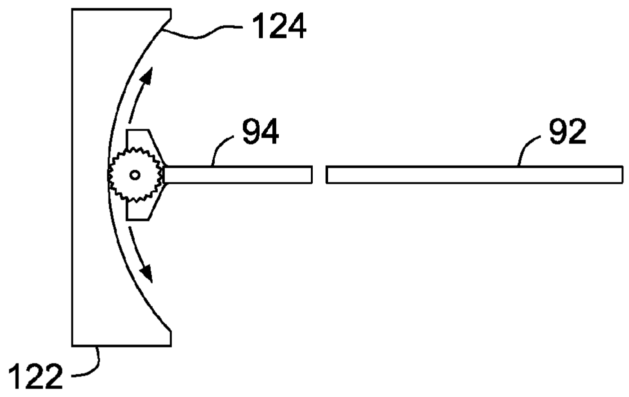
FIG. 15 is a schematic diagram of an embodiment of the invention using an arcuate path and gear or cam follower.
Figure 16:
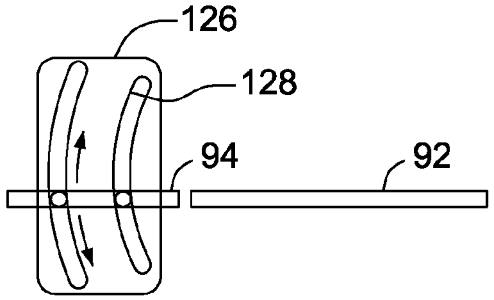
FIG. 16 illustrates the use of a multi-slotted component to control movement of the orthosis.

FIGS. 15 and 16 schematically illustrate other ways in which potentially complex movement of the second member 94 may be controlled. FIG. 15 illustrates that the cam surface may not be directly formed from a component part of either the first or second members, but instead maybe associated with some other structure. For instance, the orthosis 91 may be operatively connected to a base unit 122 having a plurality of cam surfaces 124 corresponding to different ranges of motion for related joints, such as when the orthosis 91 can be used to treat a plurality of different toes or a patient. Once the orthosis 91 is placed on the patient, the second member 94 will be positioned to securely hold one of the toes on the patient's foot and to engage with the cam surface 124 corresponding to that toe.

FIG. 16 shows that multiple cam surfaces or slots 126 may be formed in a side panel 128. The side panel 128 may have a sliding engagement of the second member 94. As the second member 94 moves, the engagement with the side panel 128 controls position and movement. Moreover, one or more sides or edges of a slot 126 of the embodiment of FIG. 16 may be geared to allow implementation of a drive assembly 100.

Figure 17:
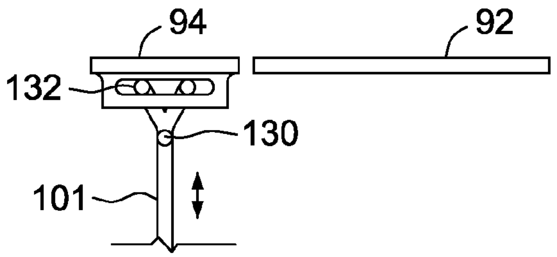
FIG. 17 illustrates an embodiment of the invention where linear movement of a component is translated into rotational and translational movement of another component of the orthosis.

FIG. 17 illustrates an embodiment where movement of at least part of a linkage 101 may be linear, but when combined with a rotational pivot 130, sliding slot 132, and possibly other components or combinations described herein, the net effect on the second member 94 is once again a controlled movement in a desired manner.

The components of the present invention are rigid members made of, for example, aluminum, stainless steel, polymeric, or composite materials. The member and extensions are sufficiently rigid to transmit the necessary forces. It should be understood that any material of sufficient rigidity might be used. For example, some components can be made by injection molding. Generally, for injection molding, tool and die metal molds of the components are prepared. Hot, melted plastic material is injected into the molds. The plastic is allowed to cool, forming components. The components are removed from the molds and assembled.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such instance, the device can be used as a positioning device for use in imaging devices, such as a MRI device. It is also contemplated that the device can be used as a positioning device for use during surgical procedures, where it may be necessary to adjust and hold the position of the joint.

All references cited herein are expressly incorporated by reference in their entirety.

It will be appreciated by persons skilled in the art that the present invention is not limited to what has been particularly shown and described herein above. For example, although the examples presented identify the toe joint, the present invention can be used for any joint in the body of the patient. In addition, unless mention was made above to the contrary, it should be noted that not all of the accompanying drawings are to scale. A variety of modifications and variations are possible in light of the above teachings without departing from the scope and spirit of the invention, which is limited only by the following claims.

What is claimed is:

1. An orthosis for stretching tissue around a foot and a toe, the orthosis comprising:
- a first member affixable to the foot and including a first extension member extending therefrom;
- a second member affixable to the toe and including a second extension member and configured to stretch tissue of one toe joint individually; and
- a drive assembly configured to move the second member.

2. The orthosis of claim 1 wherein the second extension member comprises an elongated curved shape.

3. The orthosis of claim 2 wherein the curved shape has a constant radius of curvature.

4. The orthosis of claim 2 wherein a curved shape has a variable radius of curvature allowing the axis of rotation to change as the first extension member moves along the curved shape.

5. The orthosis of claim 2 wherein the first member includes a cuff for engaging a surface of the foot and the cuff is rotatably and linearly adjustable with respect to the first member as the first extension member moves along the curved shape.

6. The orthosis of claim 1 further comprising an orthosis axis of rotation coinciding with a joint axis of rotation defined by relative movement between the toe and foot.

7. The orthosis of claim 6 wherein the location of the orthosis axis of rotation of movement between the first and second members is not constant as the first extension member moves along an elongated shape.

8. The orthosis of claim 1 wherein the first and second members move about a fixed axis of rotation.

9. The orthosis of claim 1 wherein the second member further comprises a base and a sliding contact surface that allows for relative movement between the toe and the base of the second member.

10. The orthosis of claim 1 further comprising means for securing the foot to the first member and means for securing the toe to the second member.

11. The orthosis of claim 1 wherein the second member includes a cuff for engaging a surface of the toe, the cuff is rotatably and linearly adjustable with respect to the second member for selective toe attachment.

12. An orthosis for stretching tissue around a foot and a toe, the orthosis comprising:

a first member affixable to the foot and including a first extension member; and a second member affixable to the toe and including a second extension member comprising an arcuate shaped surface extending therefrom, wherein the second extension member is operatively connected to the first extension member so that relative movement between the first and second members is determined by movement along the arcuate shaped surface.

13. An orthosis for stretching tissue around a foot and a toe, the orthosis comprising:

a first member affixable to the foot and including a first extension member extending therefrom;

a second member affixable to the toe and including a second extension member, the second extension member operatively connected to the first extension member to provide incremental movement between the first and second members; and a drive assembly in communication with the second extension member.

14. The orthosis of claim 13 further comprising:

a programmable control system configured to initiate or limit incremental movement between the first and second members according to predetermined parameters.

15. An orthosis for stretching tissue around a foot and a toe, the orthosis comprising:

a first member affixable to the foot and including a first extension member comprising a drive assembly extending therefrom; and a second member affixable to the toe and including a second extension member comprising an arcuate shape extending therefrom, wherein the drive assembly engages the second extension member for selectively moving the second member with respect to the first member.

16. The orthosis of claim 15 wherein the drive assembly includes a worm gear rotatably mounted therein and wherein the worm gear is manualably rotatable for selectively moving the second member with respect to the first member.

17. An orthosis for stretching tissue around a foot and a toe, the orthosis comprising:

a first member affixable to the foot and including a first extension member extending therefrom; and a second member affixable to the toe, the second member comprising a first end distal to the first member, a second end proximate to the first member, a flexible cushion, and a second extension member comprising an arcuate shape extending therefrom, the second extension member operatively connected to the first extension member so that relative movement between the first and second members is determined by movement along the arcuate shape.

18. The orthosis of claim 17 wherein the cushion comprises one or more of a spring, compressed gas, an elastic material, or a foamed material.

19. An orthosis for stretching tissue around a foot and a toe, the orthosis comprising:

a first member affixable to one of the toe or the foot;

a second member affixable to the other of the toe or the foot by a second extension member;

a drive member connected to the first member, the orthosis configured to stretch tissue of one toe joint individually.

20. The orthosis of claim 19 wherein the first member defines an arcuate shape, the curvature of the arcuate shape being convex and having a constant radius of curvature.

21. The orthosis of claim 19 wherein the first member defines an arcuate shape, the curvature of the arcuate shape being concave.

22. The orthosis of claim 19 wherein the first member includes a cuff for engaging the surface of a foot and the cuff is rotatably and linearly adjustable with respect to the first member.

23. The orthosis of claim 19 wherein the second member includes a cuff for engaging the surface of a toe, the cuff is rotatably and linearly adjustable with respect to the second member for selective toe attachment.

24. The orthosis of claim 19, wherein the first member is affixable to a foot, and the second member is affixable to the toe.

25. An orthosis for stretching tissue around a foot and a toe, the orthosis comprising:

a first member affixable to the foot and including a first extension member extending therefrom;

a second member affixable to the toe and including a second extension member;

an arcuate shape operatively communicating with the second extension member so that relative movement between the first and second members is determined by movement of the second extension member along the arcuate shape;

a drive assembly on the first extension member, the drive assembly engaging the second extension member for selectively moving the second member with respect to the first member; and a motor operatively connected to the drive assembly for selectively moving the second member with respect to the first member.

26. The orthosis of claim 25 wherein the second member further comprises a base and a sliding contact surface that allows for relative movement between the toe and the base of the second member.

27. The orthosis of claim 25 wherein the second member has a first end distal to the first member and a second end proximate to the first member and wherein the second member further comprises a cushion that allows one or both ends to flex as forces from relative movement of the first and second members are imparted to the toe.

28. An orthosis for stretching tissue around a foot and a toe, the orthosis comprising:

a first member affixable to the foot and including a first extension member extending therefrom;

a second member affixable to the toe and including a second extension member;

a drive assembly on the first extension member; and an orthosis axis of rotation offset from a joint axis of rotation defined by relative movement between the toe and foot, wherein the location of the orthosis axis of rotation of movement between the first and second members is not constant as the first extension member moves along an elongated shape.

* * * * *